(12) United States Patent
Cheng (10) Patent No.: US 10,004,844 B2
(45) Date of Patent: Jun. 26, 2018

(54) AUTOMATIC FAT GRAFT INJECTION DEVICE WITH NAVIGATION SYSTEM

(71) Applicant: Ming-Huei Cheng, Taipei (TW)

(72) Inventor: Ming-Huei Cheng, Taipei (TW)

(73) Assignee: CHANG GUNG MEMORIAL HOSPITAL, LINKOU, Taoyuan (TW)

( * ) Notice: Subject to any disclaimer, the term of this patent is extended or adjusted under 35 U.S.C. 154(b) by 913 days.

(21) Appl. No.: 13/871,118

(22) Filed: Apr. 26, 2013

(65) Prior Publication Data

US 2013/0310748 A1 Nov. 21, 2013

(30) Foreign Application Priority Data

May 18, 2012 (TW) .............................. 101117892 A (51) Int. Cl.
*A61M 1/00* (2006.01)
*A61M 5/142* (2006.01)
*A61B 17/00* (2006.01)

(52) U.S. Cl.
CPC ... *A61M 5/142* (2013.01); *A61B 2017/00792* (2013.01); *A61B 2017/00969* (2013.01)

(58) Field of Classification Search
CPC ......... A61M 5/142; A61B 2017/00792; A61B 2017/00969
USPC ....................................................... 604/151
See application file for complete search history.

(56) References Cited

U.S. PATENT DOCUMENTS

| | | |
|---|---|---|
| 3,539,150 A | 11/1970 | Conrad et al. |
| 4,299,221 A | 11/1981 | Phillips et al. |
| 4,504,266 A | 3/1985 | Harle |
| 5,224,929 A | 7/1993 | Remiszewski |
| 5,823,993 A * | 10/1998 | Lemelson ............ G01R 33/561 128/898 |
| 5,848,988 A * | 12/1998 | Davis .................... A61M 5/172 604/65 |
| 5,911,700 A | 6/1999 | Mozsary et al. |
| 6,428,504 B1* | 8/2002 | Riaziat .................. A61N 1/327 604/65 |
| 6,790,198 B1* | 9/2004 | White .................. A61M 5/142 604/151 |
| 2003/0105422 A1 | 6/2003 | Gonon et al. |
| 2007/0156161 A1* | 7/2007 | Weadock ........... A61B 10/0275 606/170 |
| 2009/0177081 A1* | 7/2009 | Joskowicz ............. A61B 90/13 600/426 |
| 2009/0181104 A1 | 7/2009 | Rigotti et al. |

(Continued)

FOREIGN PATENT DOCUMENTS

CN 1741828 A 3/2006

*Primary Examiner* — Edelmira Bosques (74) *Attorney, Agent, or Firm* — Bacon & Thomas, PLLC (57) ABSTRACT

The present invention relates to a fat graft injection device, which comprises: an injection unit having a connection end and a terminal; The injection unit is operated by robotic arm system in controlled speed, multiple layers, multiple lines, a storage unit connected to the injection unit; and a pump unit connected to the storage unit, wherein the storage unit is between the injection unit and contains fat grafts. Fat grafts in the storage unit are injected into the subcutaneous layer through the injection unit by the pump unit with the guiding of navigation system, thus completing the fat graft injection, with accurate and effective, manner without exhausted back and forth surgeon's arm movement.

10 Claims, 8 Drawing Sheets

(56) References Cited

U.S. PATENT DOCUMENTS

2011/0015567 A1\* 1/2011 Azar ................... A61M 5/204
  604/70
2011/0202014 A1\* 8/2011 Mutzbauer ............ A61K 31/00
  604/241

\* cited by examiner

AUTOMATIC FAT GRAFT INJECTION DEVICE WITH NAVIGATION SYSTEM

CROSS REFERENCE TO RELATED APPLICATION

This application claims the benefits of the Taiwan Patent Application Serial Number 101117892, filed on May 18, 2012, the subject matter of which is incorporated herein by reference.

BACKGROUND OF THE INVENTION

1. Field of the Invention

The present invention relates to a fat graft injection device, and particularly to an automatic fat graft injection device which comprises an injection unit, a storage unit, and a pump unit.

2. Description of Related Art

Autologous fat transplantation technique involves the following steps: the liposuction of an individual's own subcutaneous fat; first to take out autologous fat followed by the extraction and purification of the obtained fat in a sterile condition; and the transplantation by injecting fat grafts to depression or emaciated areas where desired, either congenital or acquired.

In the early period, autologous fat transplantation is not popular became the low fat graft survival and overly high autologous absorptivity due to immaturity of technique and processes. Currently, with the advance of fat graft technique, the tools are also improved correspondingly and with the aid of fat graft survival techniques, autologous fat transplantation is gradually being widely used.

Nevertheless, in the current fat graft, the fat in the syringe is injected into the targeted portion manually. In addition, the fat graft process involves extremely delicate and precise positioning and quantification. Therefore, if the injection dosages are not consistent, excess fat grafts may be overlappingly filled into the targeted area, resulting in unevenness of skin and fat necrosis. Also, when there is a slight error in injection position, the survival of the fat graft may be low, and furthermore, excessive pressure may cause more fat graft necrosis when the pressure is unevenly applied. Thus, a slight mistake may lead to poor blood circulation for the injected fat grafts, thereby causing suppuration, inflammation, or calcification at the affected region. Accordingly, there is an increased risk of surgical failure if all the surgical conditions are solely relied on manual operation.

Therefore, to solve the above-mentioned problems, what is needed in the art is to develop an automatic fat graft injection device to allow fixed orientation, quantification, and constant pressure, thereby increasing survival of fat grafts and relieving considerable physical and mental fatigue of the surgeon during surgery, as well as preventing surgical errors.

SUMMARY OF THE INVENTION

An object of the present invention is to provide a fat graft injection device in which a pump unit is used to replace a traditional syringe. The pump unit is automatically controlled to inject the fat graft into the adipose layer in a constant quantity and pressure to maintain the flatness of skin, keeping the fat graft at the right position for access to blood circulation to increase survival.

To achieve these objects, the present invention provides a fat graft injection device, comprising: an injection unit having a connection end and a terminal; a storage unit connected to the injection unit; and a pump unit connected to the storage unit between the injection unit and the pump unit; wherein the storage unit contains fat graft therein, and the fat graft in the storage unit is injected into the adipose layer through the injection unit by the pump unit, thus completing the fat graft injection.

In the fat graft injection device of the present invention, the terminal of the injection unit comprises at least one or more through holes. There may be a plurality of through holes disposed on a single side of the injection unit along a one-dimensional path, and furthermore, there may also be at least one through hole on the tube walls surrounding the terminal of the injection unit, and a through hole disposed on the top of the terminal of the injection unit. In addition, the injection unit is tubular to provide delivery of fat, that means, the fat is introduced into the adipose layer through the injection unit and then via the through holes. Depending on the different positions, the fat amount required for graft may vary. For example, for facial areas, the fat dosage may be usually merely 10 ml to 50 ml, while for breast areas, the fat dosage may be about 50 ml to 500 ml. Thus, the injection unit may be designed with various pipe diameters, different numbers of the through holes, diameters of the through holes, and so on, to cope with the demand for different dosages.

The storage unit of the fat graft injection device according to the present invention is used to store fat grafts obtained from autologous liposuction after a purification process (such as centrifugation). Such fat grafts have fat regenerative capacity. In addition, the storage unit further comprises a case formed of a rigid material to serve as a holding part to protect and cover the storage unit therein.

Furthermore, the storage unit of the fat graft injection device according to the present invention further comprises a storage unit adjusting element to control the flow rate of fat graft by regulating the diameter for fat graft exit in the storage unit. The storage unit adjusting element may be disposed anywhere, as long as convenient for user's operation. The storage unit adjusting element may be in a form of a turning button, a push button, or a push bar, preferably a turning button or a push bar, and more preferably a push button.

Also, the pump unit of the fat graft injection device according to the present invention is used to provide a propulsive force to drive the fat in the storage unit forward into the injection unit. As such, the fat graft is delivered by the injection unit through the holes to a desirable position in the adipose layer. In addition, the pump unit further comprises a pump unit adjusting element to control the operation of the pump unit. With the pump unit adjusting element, the switch of the pump unit can be controlled to thereby, regulate the pressure supplied. An increase in pressure may increase the amount of fat grafts entering the adipose layer, while a decrease in pressure may reduce the amount of fat grafts entering the adipose layer. The pump unit adjusting element may be disposed anywhere, as long as convenient for user's operation, and preferably on the case of the storage unit. The pump unit adjusting element may be in a form of a turning button, a push button, or a push bar, preferably a turning button or a push bar, and more preferably a push button. In addition, the pump unit adjusting element further comprises a control chip which is a voice control chip or a touch control chip to achieve the object of regulating the switch of the pump unit and the pressure supply in a voice or touch manner.

Furthermore, the fat graft injection device of the present invention further comprises a microprocessor connected to the storage unit and the pump unit in a wireless or wired manner, to control the operation state of the entire fat graft injection device and regulate the parameters of each component. The microprocessor further comprises a sensing unit which may be a "Navigation system" like device a three-dimensional scanner, an ultrasonic detector, a photosensor, a thermal sensor, a camera, or the like, to provide positioning information. Preferably, a typical three-dimensional scanner and an ultrasonic detector are used to serve as the sensing unit to provide image signals effectively, determine the direction of a designated point and the depth and thickness of an adipose layer, and confirm the site to be injected.

In addition, the fat graft injection device of the present invention may further comprise a power supply unit, wherein the power supply unit may be an external power supply unit which may connect to a power supply through a wire extended from the fat graft injection device. Furthermore, the power supply unit may also be a power supply unit built-in the fat graft injection device, such as a battery.

In the fat graft injection device according to the present invention, a robotic arm connected to the storage unit is further comprised to rotate and move the injection cannula unit multidirectionally. The fat graft injection device employs a robotic arm to replace manual effort of the surgeon during surgery to decrease the load of the surgeon. The robotic arm of the present invention controls the manner of movement and rotation of injection cannula unit. Thereby, the robotic arm may also adjust the operation process of direction alteration, movement, and rotation with the coordination of the navigation system.

In the fat graft injection device of the present invention, a servo motor is further included as a controller for the fat injection to control a switch unit (such as an automatic valve, a revolvers, a rotatable disk, or the like) which is connected and controls the injection unit to inject fat in a form of successive batch. Such a servo motor connected to a computer and acts following the instruction from the computer program. Alternatively, the servo motor self may serve as a dispenser to control the injection in a form of successive batch.

In an embodiment, the navigation system according to the present invention may include a camera, a wireless unit (e.g. radio frequency or blue tooth), or a processor to position the probes more precisely, and then a series of electrical signals may be obtained by the camera, processed by the processor, and transmitted through the wireless unit. Such that, the area and depth for fat injection thus be defined, and then the robotic system with particular size and the number of the side hole may be calculated and planed by using the series of electrical signals to do fat injection.

Before the surgery is performed, fat position should be investigated with a computer tomography (CT) system or a 3-Dimentional digital camera to determine the area for fat injection. After characteristics of the internal structure of an object such as dimensions, shape, internal defects, and density are readily available from CT images, or appearance images obtained from the camera, these obtained images are processed by a computer programming for 3D image modeling, and 3D surface topology. The robotic arm automatically moves to the specific position in 3 directions: latitudinal direction, longitudinal direction, and transverse direction (horizontal direction) according to the obtained 3D surface topology of a computer programming.

In addition, the automatic fat graft injection device according to the present invention may be operated combining with a robotic system to further overcome the limitations of traditional fat grafting surgery and improve the effectiveness and accuracy.

In the present invention, according to the obtained 3D surface topology of a computer programming and the obtained area, the thickness and the volume, multiple layers, number of incisional sites, positions of injection routes, moving speeds of an injection unit in the adipose layer, and quantity/time for the fat injection surgery can be calculated automatically by computer programming. In result, the fat injection using the automatic fat graft injection device of the present invention is automatically performed in the form of stratification with a specific multiple layers, number of incisional sites, injection routes, moving speeds of an injection unit in the adipose layer, and quantity/time by computer programming, wherein the fat injection at each of the incisional site in the same layer may distribute evenly and smoothly, and achieve the predictive goals.

In summary, the present invention provides an automatic fat graft injection device including a pump unit and a storage unit used to store fat, wherein a navigation system (such as a three-dimensional scanner and an ultrasonic detector) of a microprocessor is used to detect the adipose layer and to inject fat graft to the recipient site in need little by little in a one-dimensional direction in multiple lines, multiple layers. Also, the fat graft amount and the pressure of each injection can be automatically controlled by the pump unit to achieve the object of precise and uniform fat graft, thereby maintaining the higher survival rate, flatness of skin and reducing manual efforts.

BRIEF DESCRIPTION OF THE DRAWINGS

The above and other objects, features and other advantages of the present invention will be more clearly understood from the following detailed description taken in conjunction with the accompanying drawings, in which:

FIG. 7A shows a schematic view of positioning and layout of the site for fat injection. Before the surgery is performed, the area for fat graft injection should be disinfected, and then a positioning needles for measuring the x, y plane is inserted at this area. The positioning needles inserted at the X mark to determine the area for fat graft injection, and the insertion depth is set by a microprocessor unit, wherein the positioning needle is further installed with at least one sensor connected to the microprocessor unit to transmit signals with each other.

FIG. 7B shows an enlarged schematic view of the site for fat injection. Four positioning needles 80 are inserted at the area, which fat graft through the dermal layer 91 to the adipose layer 92.

DETAILED DESCRIPTION OF THE PREFERRED EMBODIMENT

In the following description, numerous specific details are set forth to provide a thorough understanding of embodiments of the present disclosure. However, one having an ordinary skill in the art will recognize that embodiments of the disclosure can be practiced without these specific details.

Observation of Fat Position

Before the surgery is performed, the recipient site should be accessed with a computer tomography (CT) system or a 3-Dimantional digital camera to determine the area for fat injection. Computer tomography (CT) is a powerful nondestructive evaluation technique for producing 2-D and 3-D cross-sectional images of an object from flat X-ray images. After characteristics of the internal structure of an object such as dimensions, shape, internal defects, and density are readily available from CT images, or appearance images obtained from the 3-D camera, these obtained images are processed by a computer programming for 3D image modeling, or 3D surface topology. The robotic arm 5 automatically moves to the specific position in 3 directions: latitudinal direction, longitudinal direction, and transverse direction (horizontal direction) according to the obtained 3D surface topology of a computer programming.

Embodiment 1

Figure 1:
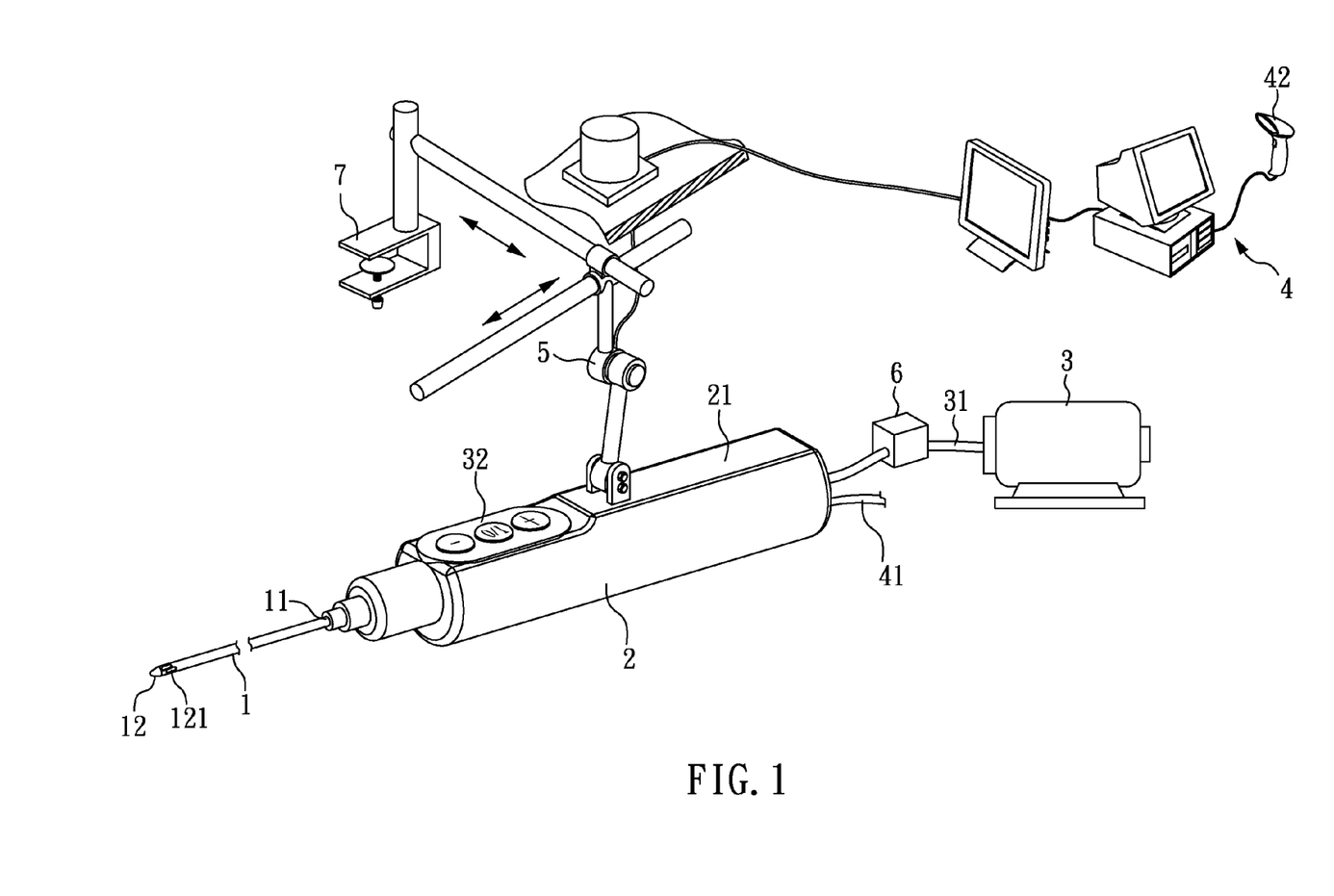
FIG. 1 shows a schematic view of the fat graft injection device contains of injection unit, control panel, storage unit of Embodiment 1 according to the present invention. The fat graft injection device of this embodiment comprises an injection unit 1, a storage unit 2, a pump unit 3, a computer 4 with a detector 42, a robotic arm 5, a servo motor 6, an operation table fixation 7, and a power supply unit (not shown), wherein the injection unit 1 is tubular and has a connection end 11 and a terminal 12.
Figure 2A:
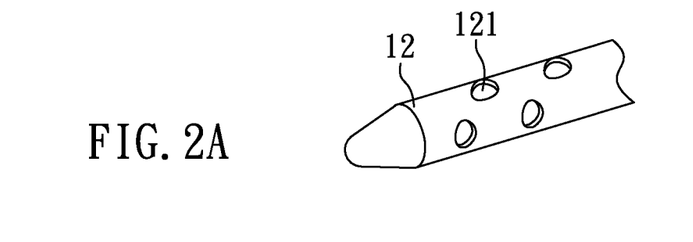
FIGS. 2A-2C shows a schematic view of the injection unit may have different sizes and distributed of side holes. Embodiment 1 according to the present invention, wherein the terminal 12 may be cylindrical or beak-like and may have one or more side holes 121 through which the fat graft can be injected into the adipose layer.
Figure 2B:
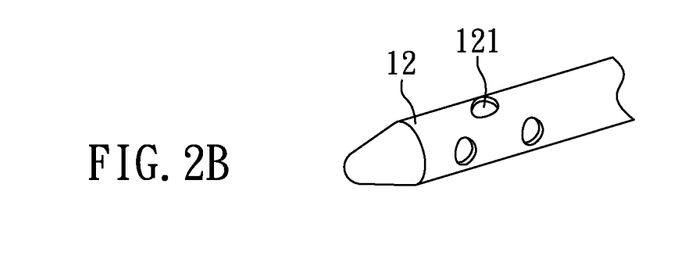
Figure 2C:
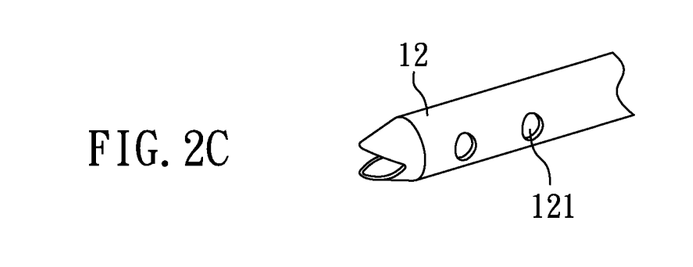

Referring to FIG. 1, which shows a schematic view of the fat graft injection device of Embodiment 1 according to the present invention. The fat graft injection device of this embodiment comprises an injection unit 1, a storage unit 2, a pump unit 3, a computer 4 with a detector 42, a robotic arm 5, a servo motor 6, an operation table fixation 7, and a power supply unit (not shown), wherein the injection unit 1 is tubular and has a connection end 11 and a terminal 12. As shown in FIGS. 2A-2C, the terminal 12 may be cylindrical or beak-like and may have one or more side holes 121 through which the fat graft can be injected into the adipose layer. In addition, the storage unit 2 connected to the injection unit 1 is used to store fat grafts obtained from the purified autologous fat graft. Also, the storage unit may further comprise a case 21 formed of a rigid material to serve as a holding part of the fat graft injection device according to the present invention to protect and cover the storage unit 2 therein.

The pump unit 3 is connected to the storage unit 2 via a pipeline 31, and the storage unit 2 is disposed between the injection unit 1 and the pump unit 2, wherein the pipeline 31 is used to provide a propulsive force to drive the fat graft in the storage unit 2 into the injection unit 1. As such, the fat graft is delivered by the injection unit 1 through the side holes 121 to a desirable area in the adipose layer. In addition, the storage unit 3 further comprises a pump unit control panel 32 disposed on the case 21 of the storage unit 2 in a form of a combination of buttons comprising a switch button, a pressure increase button, and a pressure decrease button, to control the operation of the pump unit 3. The switch button of the control panel 32 can turn on the pump unit 3 in a pulse manner to provide a positive pressure to inject the fat grafts from the storage unit 2 into the adipose layer through the injection unit 1. Also, the applied pressure can be regulated by the pressure increase button and the pressure decrease button, and an increase in pressure may increase the amount of fat grafts entering the adipose layer, while a decrease in pressure may reduce the amount of fat grafts entering the adipose layer. However, the storage unit 2 and the pump unit 3 can be connected by an electrical connection (not shown), to control the signal transmission therebetween. Also, the storage unit 2 of this embodiment is connected to a power line 41 extending to the power supply unit (not shown) to provide electric power source of this embodiment.

In this Embodiment, the robotic arm 5 is connected to the injection unit 1 to rotate and move the storage unit 2, line by line, layer by layer according to X, Y axis. The robotic arm replaces manual operation and can adjust the position and angle of the storage unit 2, thereby adjusting the positions and angles of the navigation system.

In the fat graft injection device of this embodiment, a servo motor 6 is further included as a controller for the fat injection to control an automatic valve (not shown), which is connected and controls the injection unit to inject fat in a form of successive batch. Such a servo motor connected to a computer and acts following the instruction from the computer program.

Embodiment 2

Figure 3:
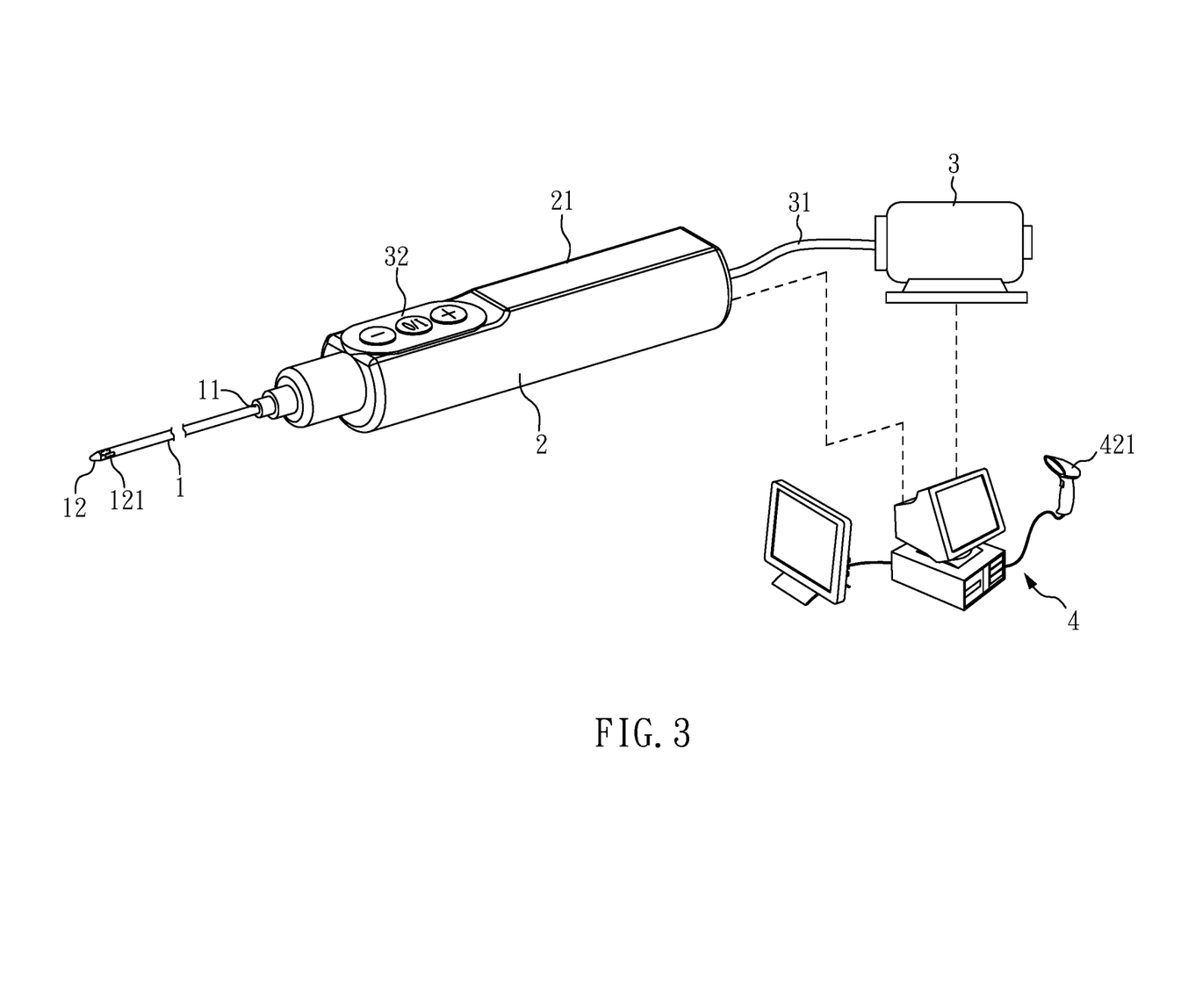
FIG. 3 shows a schematic view of the fat graft injection device with a navigation system of Embodiment 2 according to the present invention. A navigation system can be added to adjust the recipient site area and depth for fat graft injection. The fat graft injection device is substantially the same as Embodiment 1, an except navigation system that this embodiment further comprises a microprocessor 4 connected to the storage unit 2 and the pump unit 3 in a wireless or wired manner to transmit signals with each other, to control and show each parameter in the fat graft injection device of this embodiment.

Referring to FIG. 3, which shows a schematic view of the fat graft injection device of Embodiment 2 according to the present invention. The fat graft injection device is substantially the same as Embodiment 1, except that this embodiment further comprises a microprocessor 4 connected to the storage unit 2 and the pump unit 3 in a wireless or wired manner to transmit signals with each other, to control and show each parameter in the fat graft injection device of this embodiment. The microprocessor 4 also connects to the computer. Furthermore, the microprocessor 4 further comprises a sensing unit 421 which may be a three-dimensional scanner for positioning and confirming the depth and thickness of an adipose layer, and transmitting image signals to be processed by the microprocessor 4, thereby providing information of the designated position for a surgeon to determine the position of fat grafting.

Embodiment 3

Figure 4:
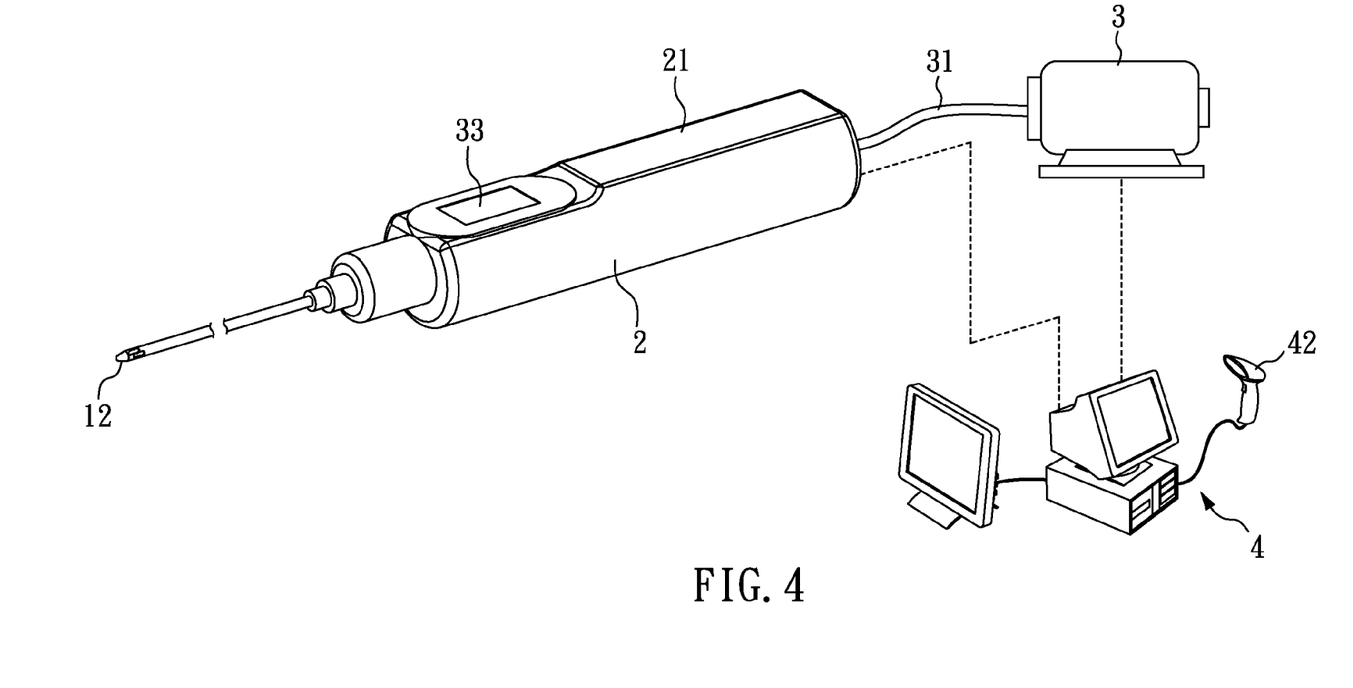
FIG. 4 shows a schematic view of the fat graft injection device of Embodiment 3 according to the present invention. The fat graft injection device is substantially the same as Embodiment 2, except that the pump unit control panel of the this embodiment is a control chip 33 for regulating the operation of the pump unit 3 in a touch manner.

Referring to FIG. 4, which shows a schematic view of the fat graft injection device of Embodiment 3 according to the present invention. The fat graft injection device is substantially the same as Embodiment 2, except that the pump unit control panel of the this embodiment is a control chip 33 for regulating the operation of the pump unit 3 in a touch manner.

Embodiment 4

Figure 5A:
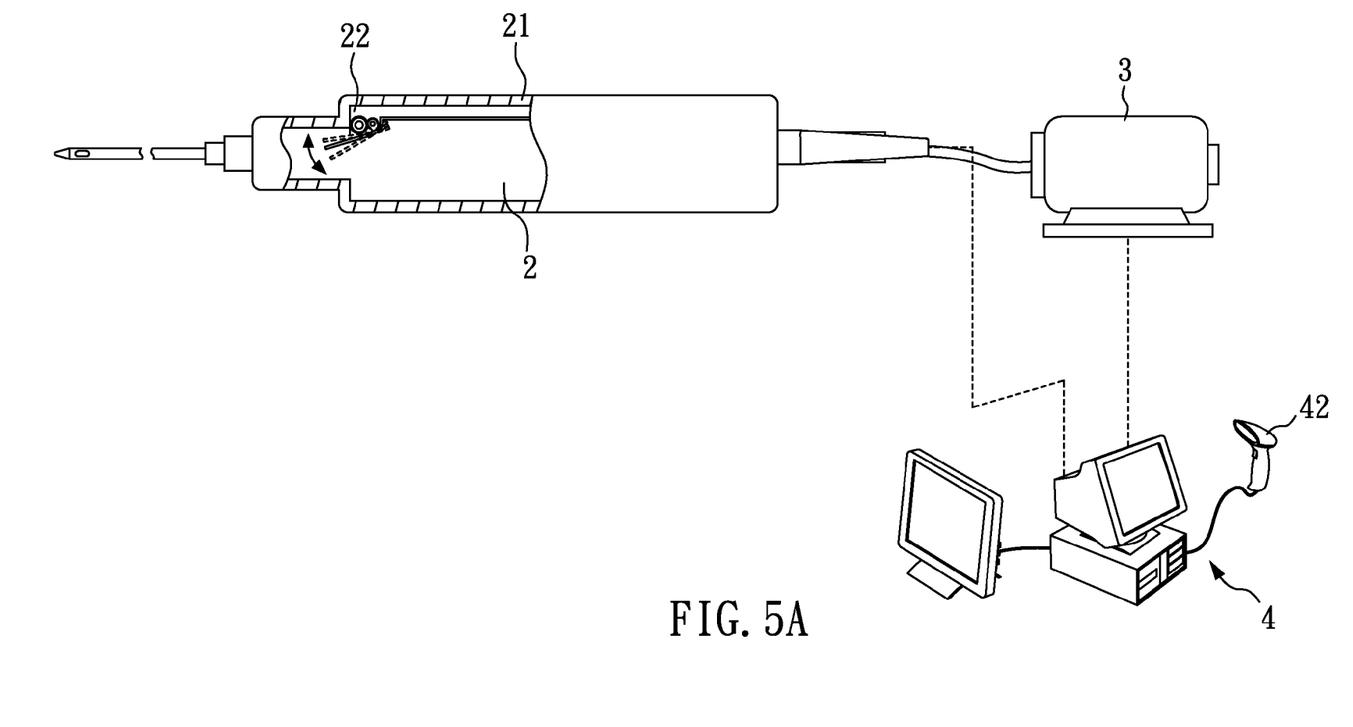
FIG. 5A shows a schematic view of the fat graft injection device of Embodiment 4 according to the present invention.
Figure 5B:
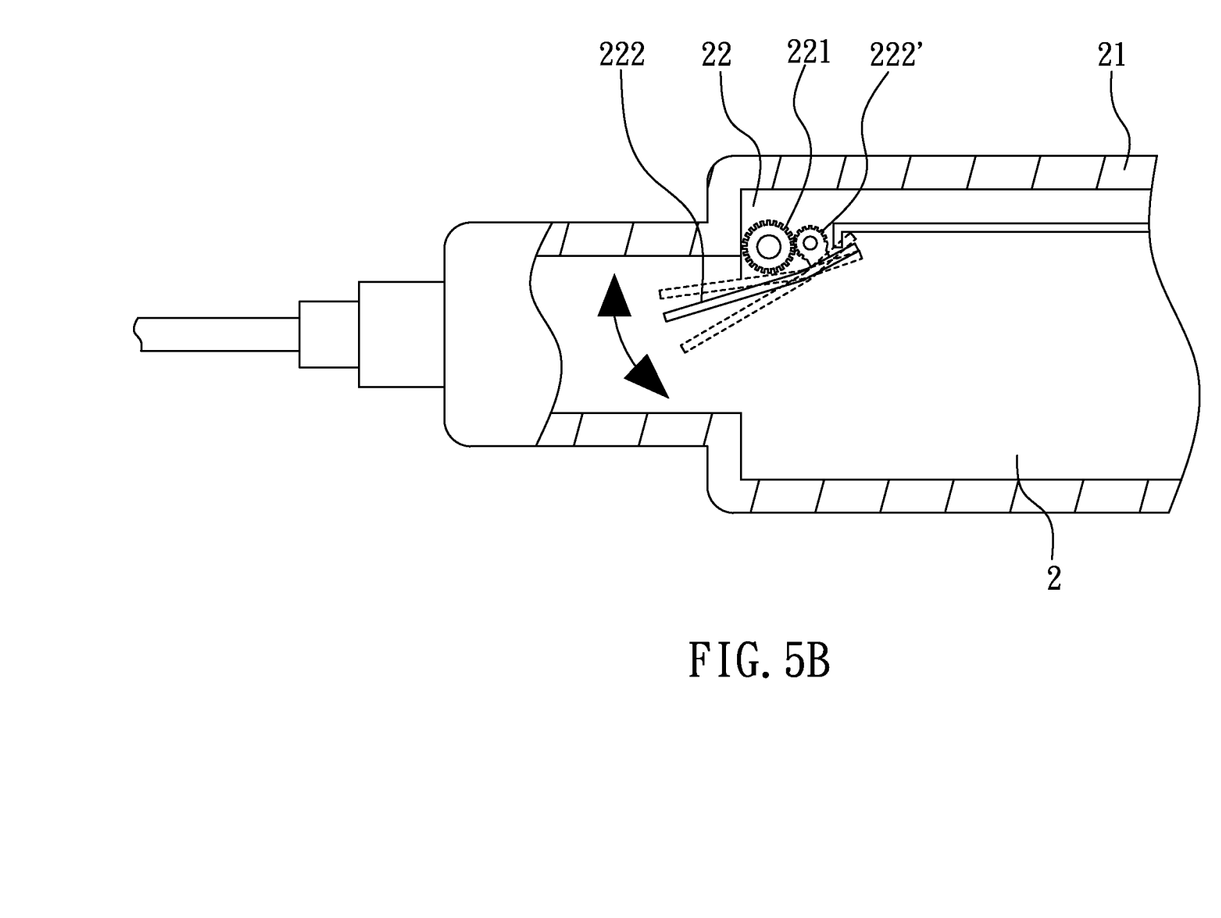
FIG. 5B shows an enlarged schematic view of the storage unit adjusting element of Embodiment 4 according to the present invention. The fat graft injection device is substantially the same as Embodiment 2, except that this embodiment uses a storage unit adjusting element 22 to control the flow rate of fat graft, in a manner of rotating a gear 221 by a turning button (not shown) to drive the rack rail 222' on a partition 222 mechanically, thereby pressing down or lifting up the partition 222 to regulate the exit diameter of the storage unit adjusting element 22 to the injection unit 1 to control the fat graft amount of each injection.

Referring to FIG. 5A, which shows a schematic view of the fat graft injection device of Embodiment 4 according to the present invention. The fat graft injection device is substantially the same as Embodiment 2, except that this embodiment uses a storage unit adjusting element 22 to control the flow rate of fat graft, in a manner of rotating a gear 221 by a turning button (not shown) to drive the rack rail 222' on a partition 222 (as shown in FIG. 5B) mechanically, thereby pressing down or lifting up the partition 222 to regulate the exit diameter of the storage unit adjusting element 22 to the injection unit 1 to control the fat graft amount of each injection. However, the turning button adjusting element may also control the operation of a mechanical adjusting element according to the parameters set by the microprocessor 4.

Embodiment 5

Figure 6:
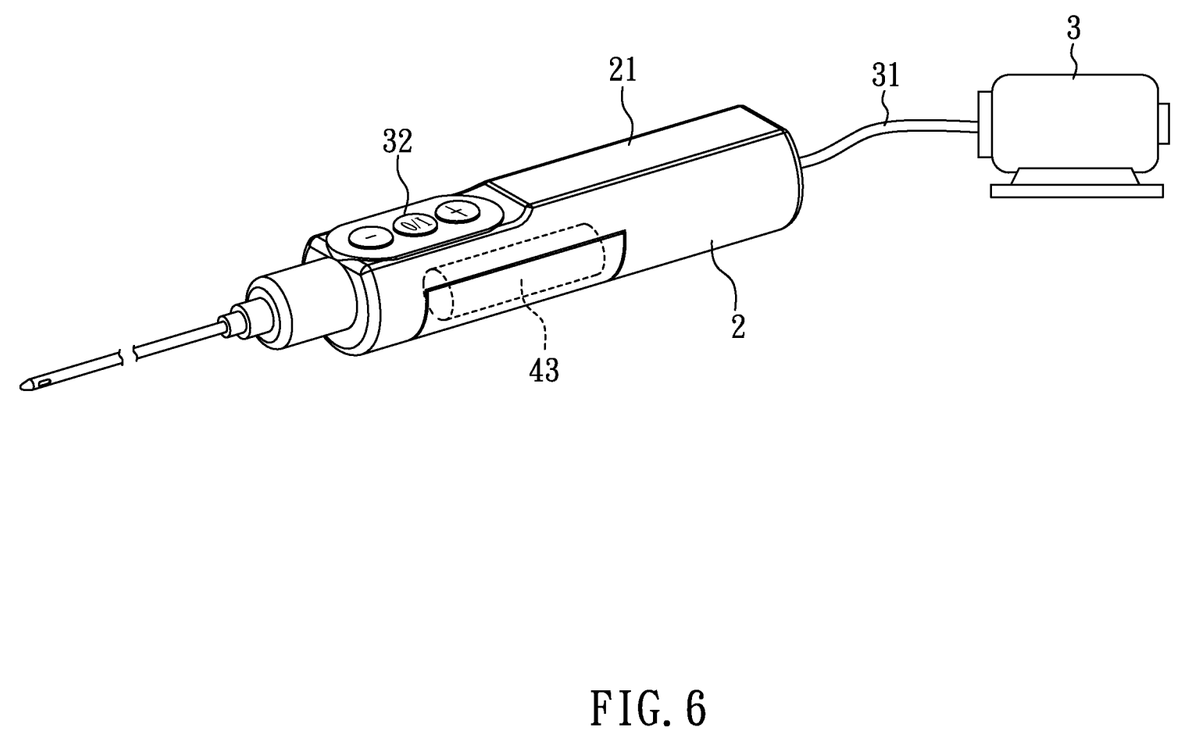
FIG. 6 shows a schematic view of the fat graft injection device of Embodiment 5 according to the present invention. The fat graft injection device is substantially the same as Embodiment 1, except that the electric power source of this embodiment is a battery 43, and thus, this embodiment has the same portability with a syringe of the traditional fat graft injection device, but surpasses the traditional syringe with its automation.

Referring to FIG. 6, which shows a schematic view of the fat graft injection device of Embodiment 5 according to the present invention. The fat graft injection device is substantially the same as Embodiment 1, except that the electric power source of this embodiment is a battery 43, and thus, this embodiment has the same portability with a syringe of the traditional fat graft injection device, but surpasses the traditional syringe with its automation.

In summary, according to the above embodiments of the present invention, the fat grafts in the storage unit are injected into the adipose layer through the injection unit by the pump unit, and the fat graft injection is performed with a syringe pushed in an automatic manner instead of manual operation. In addition, with the microprocessor, the conditions of the surgery process can be fine-tuned, to achieve a fat graft injection with multiple lines, multiple layers, equally distributed, quantification, and constant pressure, thereby increasing survival of fat grafts and relieving considerable physical and mental fatigue of the surgeon during surgery.

Figure 7A:
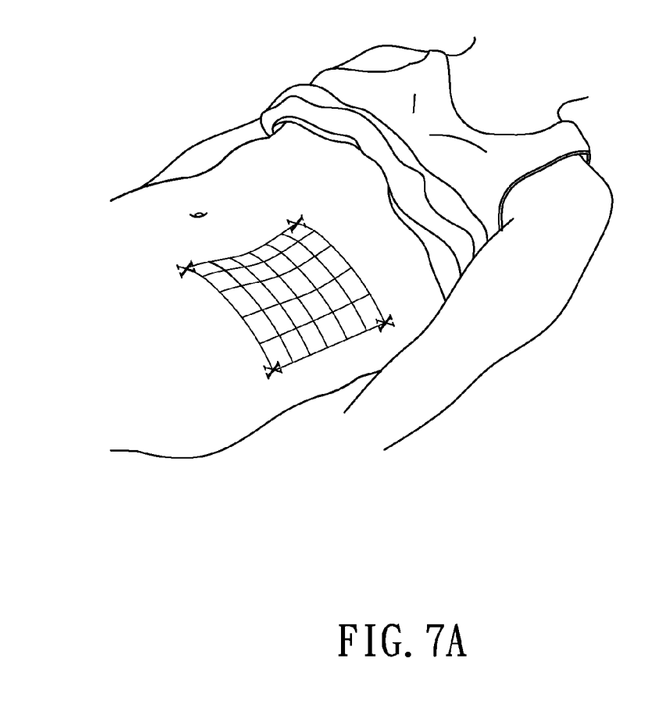
Figure 7B:
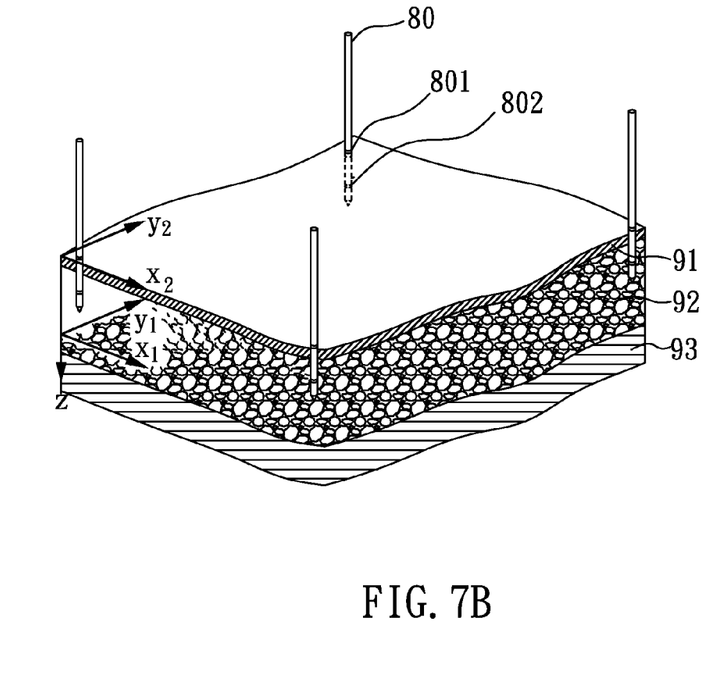

Operation Embodiment 1: Positioning of the Area and Thickness of the Recipient Site (x, y, z Axis) Before Fat Injection Before the surgery is performed, the site for fat graft injection should be disinfected, and then a positioning needle for measuring the x, y plane is inserted at this site, as shown in FIG. 7A. The following steps were comprised: 1. Insert the positioning needles (probes) to definite the area and depth of fat injection; 2. Navigation system is used to start to scan the surface of area defined for the volume and area of fat injection; 3. Micro processer (chip) calculate and make a plan for fat injection, such as area, depth, volume, speed, and required time; 4. Choose injection unit (large or small diameter with different side holes); 5. Set up the robotic system; 6. Action. The positioning needles inserted at the X mark to determine the area for fat graft injection, and the insertion depth is set by a microprocessor unit (such as a computer), wherein the positioning needle is further installed with at least one sensor connected to the microprocessor unit to transmit signals with each other. For example, referring to FIG. 7B, four positioning needles 80 are inserted at the site graft through the dermal layer 91 to the adipose layer 92. Each of the positioning needles 80 has a first positioning sensor 801 and a second positioning sensor 802, wherein a height H between the first positioning sensor 801 and the second positioning sensor 802 may be adjusted depending on the different thicknesses of the tissue. The first positioning sensor 801 is disposed between the dermal layer 91 and the adipose layer 92, and the second positioning needle sensor 802 is disposed in the space between the adipose layer 92 and the muscle layer 93. Thus, the fat graft injection device will not migrate to the muscle layer. The positioning needles 80 are used not only to determine the area for the fat graft injection, but also to decide the depth (z axis) for the fat graft injection, as well as to provide a stereotactic positioning function, to achieve automatic fat graft injection. In addition, the sensors and the guiding unit of the present invention transmit signals with each other, and the sensors may also scan the depth for fat graft injection automatically and provide instructions of the area for fat injection. Then, the x. y. and z axes are determined at the site for fat graft injection (as shown in FIG. 7B), wherein [x×y] is the area for fat graft injection, z is the depth of the fat. In addition, the distance between the four positioning needles is divided into "m" equal parts in x axis, "n" equal parts in y axis, and "k" equal parts in z axis, to lay out a grid pattern, i.e. a m×n grid pattern, in the xy plane for fat injection. "m" is using the unit of centimeter such 6 cm, m=6. Thus, the fat amount and direction for fat injection are easy to control and well distributed. Such a positioning system can be used to estimate the area (m×n), the thickness (k−1) and the volume [m×n×(k−1)], as well as the processing time for fat injection, wherein (k−1) is the thickness of the adipose layer excluding the thickness (z-axis) of the dermal layer. The reason for z-axis amount "k−1" is for preserving 1 cm away from the skin to avoid penetrating or uneven skin surface. Therefore, after the fat injection of a predetermined plane (as shown in FIG. 7B: x1, y1) is completed, another plane for fat injection (x2, y2) located at a shallower position is subsequently performed, in a manner of from deep to superficial planes along the z-axis. Therefore, the flatness of skin can be maintained after the fat injection surgery.

In the present invention, according to the obtained 3D surface topology of a computer programming and the obtained area (m×n cm$^2$), the thickness (k−1 cm) and the volume [m×n×(k−1) cm$^3$], multiple layers of stratification, a incisional site number and position, a moving speed of an injection unit 1 in the subcutaneous layer, and a quantity/time for the fat graft injection surgery can be calculated automatically by computer programming. In result, the fat injection using the automatic fat graft injection device of the present invention is automatically performed in the form of stratification with a specific layer numbers, numbers of incisional sites, injection route, a moving speed of an injection unit 1 in the adipose layer, and quantity/time by computer programming, wherein the fat injection at each of the subcutaneous layer may distribute evenly and smoothly, and achieve the predictive goals.

Although the present invention has been explained in relation to its preferred embodiment, it is to be understood that many other possible modifications and variations can be made without departing from the spirit and scope of the invention as hereinafter claimed.

What is claimed is:

1. A fat graft automatic injection device, comprising: a tubular injection unit having a connection end and a terminal, and the terminal comprises one or more through holes; a storage unit connected to the injection unit; a pump unit connected to the storage unit, and the storage unit is disposed between the injection unit and the pump unit; and a microprocessor connected to the storage unit and the pump unit to transmit signals with each other; a plurality of positioning needles, each of the positioning needles is further installed with at least one sensor connected to the microprocessor to transmit signals with each other; wherein each of the positioning needles is installed with a first positioning sensor and a second positioning sensor, to determine an area and a depth for a fat graft injection and provide a stereotactic positioning function;

and wherein the storage unit contains fat grafts therein, the microprocessor further comprises a navigation system, and the navigation system is a three-dimensional scanner.

2. The fat graft injection device of claim 1, further comprising a storage unit adjusting element.

3. The fat graft injection device of claim 2, wherein the storage unit adjusting element is a turning button, a push button, or a push bar.

4. The fat graft injection device of claim 1, further comprising a pump unit adjusting element to control the operation of the pump unit.

5. The fat graft injection device of claim 4, wherein the pump unit adjusting element is a turning button, a push button, or a push bar.

6. The fat graft injection device of claim 4, wherein the pump unit adjusting element further comprises a control chip.

7. The fat graft injection device of claim 6, wherein the control chip is a voice control chip or a touch control chip.

8. The fat graft injection device of claim 1, wherein the microprocessor is connected to the storage unit and the pump unit in a wireless or wired manner.

9. The fat graft injection device of claim 1, further comprising a robotic arm connected to the injection unit to rotate and move the injection unit multidirectionally.

10. A fat graft automatic injection device, comprising: a tubular injection unit having a tubular body, a connection end, and a terminal end, and the terminal end comprises one or more through holes; a storage unit connected to the injection unit at the connection end; a pump unit connected to the storage unit, and the storage unit is disposed between the injection unit and the pump unit and configured in a way such that fat graft contained in the storage unit is able to be forced into the tubular injection unit; and a microprocessor connected to the storage unit and the pump unit to transmit signals with each other to control operation of the fat graft automatic injection device; a plurality of positioning needles, each of the positioning needles is further installed with at least one sensor connected to the microprocessor to transmit signals with each other; and wherein each of the positioning needles is installed with a first positioning sensor and a second positioning sensor, to determine an area and a depth for a fat graft injection and provide a stereotactic positioning function; wherein the storage unit contains the fat grafts therein, wherein the microprocessor further comprises a navigation system, and the navigation system is a three-dimensional scanner configured to provide positioning information from the at least one sensor of the plurality of positioning needles to determine or adjust a depth of an injection of the fat graft.

* * * * *